(12) United States Patent
Thompson

(10) Patent No.: US 6,939,347 B2
(45) Date of Patent: Sep. 6, 2005

(54) ELECTROSURGICAL GENERATOR AND METHOD WITH VOLTAGE AND FREQUENCY REGULATED HIGH-VOLTAGE CURRENT MODE POWER SUPPLY

(75) Inventor: Richard Thompson, Centennial, CO (US)

(73) Assignee: ConMed Corporation, Utica, NY (US)

(*) Notice: Subject to any disclaimer, the term of this patent is extended or adjusted under 35 U.S.C. 154(b) by 242 days.

(21) Appl. No.: 10/299,951

(22) Filed: Nov. 19, 2002

(65) Prior Publication Data

US 2004/0095100 A1 May 20, 2004

(51) Int. Cl.[7] .............................................. A61B 18/18
(52) U.S. Cl. ........................................ 606/34; 128/898
(58) Field of Search ...................... 606/27–52; 128/898

(56) References Cited

U.S. PATENT DOCUMENTS

| | | | |
|---|---|---|---|
| 4,429,694 A | | 2/1984 | McGreevy |
| 4,438,766 A | | 3/1984 | Bowers |
| 4,479,174 A | | 10/1984 | Cates |
| 4,586,118 A | | 4/1986 | Mihalka |
| 4,658,819 A | | 4/1987 | Harris et al. |
| 4,683,529 A | | 7/1987 | Bucher, II |
| 4,685,040 A | | 8/1987 | Steigerwald et al. |
| 4,727,874 A | * | 3/1988 | Bowers et al. .............. 606/38 |
| 4,772,995 A | | 9/1988 | Gautherin et al. |
| 4,864,479 A | | 9/1989 | Steigerwald et al. |
| 4,959,764 A | | 9/1990 | Bassett |
| 4,975,823 A | | 12/1990 | Rilly et al. |
| 5,066,900 A | | 11/1991 | Bassett |
| 5,167,660 A | | 12/1992 | Altendorf |
| 5,318,563 A | | 6/1994 | Malis et al. |
| 5,372,596 A | | 12/1994 | Klicek et al. |
| 5,390,101 A | | 2/1995 | Brown |

(Continued)

FOREIGN PATENT DOCUMENTS

| | | |
|---|---|---|
| DE | 3904558 | 8/1990 |
| EP | 0136855 | 4/1985 |
| EP | 1082944 | 3/2001 |
| EP | 1157667 | 11/2001 |

OTHER PUBLICATIONS

Switch Mode Power Supplies, L5991 and L5991A: High Performance PWM Controllers, Product News 3rd edition 2000, 3 pages.
Primary Controller with Standby, ST®Publication, Aug. 2001, 4 pages.
International Search Report for the PCT application PCT/US 03/34079 which corresponds to the present U.S. application.
H. Hölscher et al., *Microcomputers in Safety Technique, An Aid to Orientation for Developer and Manufacturer*, 1986, Chapter 1–1 through 8–9.
Aspen Laboratories, Bistat Electrosurgical Unit Operator & Service Manual, 1994.
ConMed Corporation, Hyfrecator® 2000 Electrosurgical Unit Service Manual, 5 pages, 1998.
ConMed Aspen Surgical Systems, Sabre 180 Electrosurgical Unit Service Manual, 6 pages, 1994.
PCT International Preliminary Examination Report dated Dec. 13, 2004.

*Primary Examiner*—Michael Peffley
*Assistant Examiner*—Pete Vrettakos
(74) *Attorney, Agent, or Firm*—John R. Ley

(57) ABSTRACT

DC input energy is converted into DC output voltage by the use of a switched current mode high-voltage power supply. Pulses of input current are switched through a conversion transformer and the energy content of each pulse is converted into the DC output voltage. The time widths of the input current pulses are regulated relative to the DC input and output voltages, the magnitude of the current within each input current pulse, and in relation to maintaining a plurality of different selected operational conditions. The rate at which the input current pulses are converted is changed relative to the level of the DC output voltage.

22 Claims, 6 Drawing Sheets

U.S. PATENT DOCUMENTS

| | | |
|---|---|---|
| 5,418,410 A | 5/1995 | Tisinger |
| 5,757,635 A | 5/1998 | Seong |
| 5,777,503 A | 7/1998 | Faulk |
| 5,792,138 A | 8/1998 | Shipp |
| 5,793,191 A | 8/1998 | Elmore et al. |
| 5,883,793 A | 3/1999 | Farrington |
| 5,886,881 A | 3/1999 | Xia et al. |
| 5,901,054 A | 5/1999 | Leu et al. |
| 5,933,333 A | 8/1999 | Tsuji |
| 5,945,820 A | 8/1999 | Namgoong et al. |
| 6,049,471 A | 4/2000 | Korcharz et al. |
| 6,051,961 A | 4/2000 | Jang et al. |
| 6,093,186 A | 7/2000 | Goble |
| 6,127,816 A | 10/2000 | Hirst |
| 6,142,992 A | 11/2000 | Cheng et al. |
| 6,144,245 A | 11/2000 | Balogh |
| 6,215,288 B1 | 4/2001 | Ramsey et al. |
| 6,219,262 B1 | 4/2001 | Burgyan |
| 6,229,289 B1 | 5/2001 | Piovaccari et al. |
| 6,256,214 B1 | 7/2001 | Farrington et al. |
| 6,261,285 B1 | 7/2001 | Novak et al. |
| 6,294,904 B1 | 9/2001 | Hirst |
| 6,296,636 B1 | 10/2001 | Cheng et al. |
| 6,356,463 B1 | 3/2002 | Tsai |
| 6,370,051 B1 | 4/2002 | Patel |
| 6,381,150 B2 | 4/2002 | Telefus |
| 6,385,059 B1 | 5/2002 | Telefus et al. |
| 6,416,509 B1 | 7/2002 | Goble et al. |

\* cited by examiner

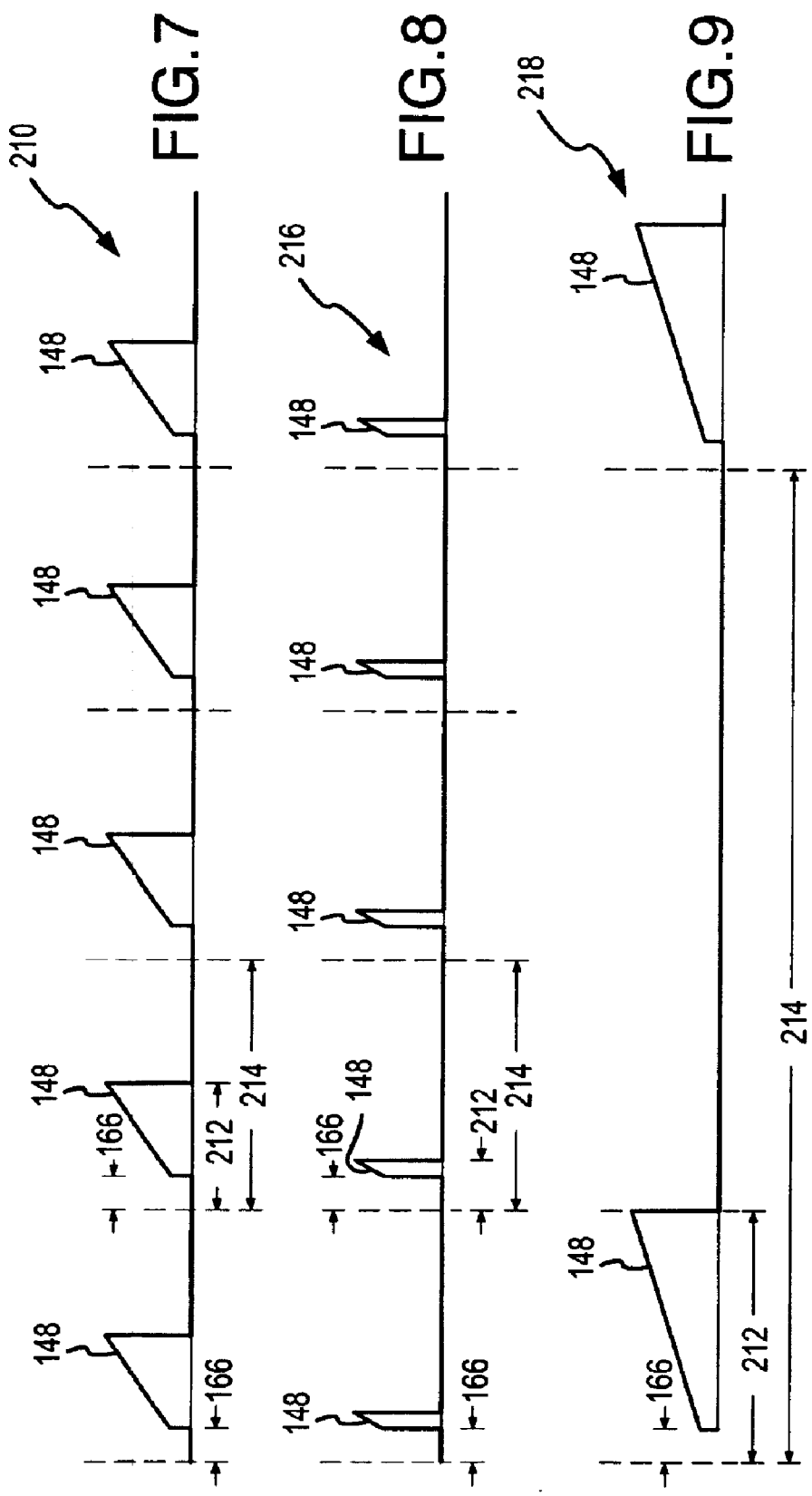

ELECTROSURGICAL GENERATOR AND METHOD WITH VOLTAGE AND FREQUENCY REGULATED HIGH-VOLTAGE CURRENT MODE POWER SUPPLY

CROSS REFERENCE TO RELATED APPLICATION

This invention and application is related to an invention for Electrosurgical Generator and Method with Multiple Semi-Autonomously Executable Functions, Ser. No. (24.346) filed concurrently herewith and assigned to the assignee of the present invention. The subject matter of this concurrently filed application is incorporated herein by reference.

FIELD OF THE INVENTION

The invention generally relates to electrosurgery, and more specifically, to a new and improved electrosurgical generator and high voltage power supply for an electrosurgical generator that regulates the high voltage power supply in relation to a selected mode of operation for the electrosurgical generator and a selected power output from the electrosurgical generator, by output voltage regulation and conversion frequency control in a switched current mode power supply, among other things, to effectively deliver electrosurgical energy to tissue under the rigorous and widely varying output power delivery conditions typical of electrosurgery.

BACKGROUND OF THE INVENTION

Electrosurgery involves applying relatively high voltage, radio frequency (RF) electrical power to tissue of a patient undergoing surgery, for the purpose of cutting the tissue, coagulating or stopping blood or fluid flow from the tissue, or cutting and coagulating the tissue simultaneously. The high voltage, RF electrical power is created by an electrosurgical generator, and the electrical power from the generator is applied to the tissue from an active electrode manipulated by a surgeon during the surgical procedure.

The amount and characteristics of the electrosurgical power delivered to the patient is determined by the surgeon and depends on the type of surgical procedure to be performed and the amount of electrosurgical output power required, as well as the tissue characteristics of the patient. Selecting the cutting mode of operation causes the electrosurgical generator to continuously deliver relatively high RF power of moderate voltage. Selecting the coagulation mode of operation causes the electrosurgical generator to repetitively deliver relatively short bursts of high voltage, resulting in a relatively low average output power delivery. Selecting the "blend" mode of operation causes the electrosurgical generator to deliver output power having characteristics which are related to both cutting and coagulation. The blend mode of operation involves repetitively delivering relatively longer bursts of somewhat lower voltage RF output power, resulting in a relatively moderate average output power delivery. In the cut mode, for example, the continuous power output may be as high as 300 watts with an open circuit output voltage in the neighborhood of 2,000 volts peak to peak. In the coagulation mode, the bursts may reoccur at a frequency of approximately 30 kHz, have a time duration of approximately 3 microseconds, and have a peak to peak voltage of approximately 10,000 volts. A typical blend mode will involve bursts at the same frequency of approximately 30 kHz, but with time duration of approximately 5–7 microseconds and at a peak to peak voltage of approximately 4,000 volts. The higher voltage required for coagulation and blend is necessary to cause arcs of electrical power to jump from the active electrode to the tissue. Lower output voltage is used for cutting because electrical arcing is not as important or necessary for cutting.

The electrosurgical generator should also have the capability to deliver these types of RF electrosurgical power under a wide variety of different and rapidly changing output conditions. The impedance of the tissue into which the RF output power is delivered may change substantially from point-to-point as the active electrode is moved during the surgical procedure. For example, a highly fluid-perfused tissue such as the liver may exhibit a resistance or impedance in the neighborhood of 40 ohms. Other tissues, such as skin which has very little moisture content, or the marrow of bone because of its physiology, have impedance in the neighborhood of 1000–2000 ohms. Average tissue impedances range in the neighborhood of approximately 500 ohms, although the fat or adipose content of the tissue increases its impedance.

The power transfer or delivery capabilities of an electrosurgical generator, like any other power amplifier, depends on the output load characteristics into which the power is transferred. The maximum power transfer occurs when the internal impedance characteristic of the power amplifier is matched to the external impedance into which it delivers power. Since the internal impedance characteristic of the usual electrosurgical generator cannot be matched to the widely varying tissue impedance into which the electrosurgical power must be transferred, the electrosurgical generator should have the capability to deliver relatively higher amounts of power to compensate for the usual mismatch between the internal generator impedance and the widely varying values of the external tissue impedance, and to do so on an almost instantaneously changing basis as the surgeon moves through and works with the different types of tissues at the surgical site.

Further still, an electrosurgical generator must deliver the RF electrosurgical power under tightly regulated and precisely controlled conditions. Any attempt to meet the rapidly changing power requirements cannot be accompanied by excessive over-control to the point where the output RF electrosurgical power causes damage to the tissue or injury to the patient or surgical personnel. Rapid and reliable control over the delivered power is essential to safe and dependable performance of the surgical procedures.

Very few, if any, electrosurgical generators have the capability to meet all of these requirements, regardless of how well these requirements are understood. Indeed, almost no other electrical amplifier or power supply is subject to such widely varying requirements.

To deliver and regulate the RF electrosurgical output power, the typical electrosurgical generator uses a high voltage power supply to convert conventional commercial mains alternating current (AC) into direct current (DC) at a fixed voltage, and an RF amplifier output section which creates the RF electrosurgical power. The RF amplifier output section generates the RF output waveform, creates the bursts or duty cycle delivery of the RF waveform, and regulates the output power of the RF electrosurgical waveform delivered. It is typical that the high voltage power supply changes the amount of DC voltage delivered to the RF amplifier output section depending upon the mode of electrosurgical operation selected. For example, the high voltage power supply may deliver a DC output voltage of approximately 20–150 volts during the cut mode and approximately 50–300 volts during the coagulation mode.

The most prevalent type of RF amplifier output section used in an electrosurgical generator is a resonant circuit, in which a primary winding of an output transformer is connected to a capacitor to form the resonant circuit. Energizing pulses of electrical energy are delivered to the resonant circuit, and the resonant circuit responds to the energizing pulses by oscillating at a predetermined frequency established by the values of its inductance and capacitance. The transformer transforms the oscillations into the RF electrosurgical output waveform. The timing for the delivery of the energizing pulses creates either the continuous or the burst-like duty cycle delivery of the RF output waveform. The power or energy of the RF output waveform is controlled by the amount of power contained within each energizing pulse.

The amount of power contained in each energizing pulse is determined by the voltage of that pulse and the time width or on-time duration of the energizing pulse. The voltage of the energizing pulse is established by the high voltage power supply, because the DC output voltage from the high voltage power supply is used in creating the energizing pulse. Control over the on-time width of the energizing pulse is achieved by rapidly-responding digital logic circuits. Another type of RF output section sometimes used in electrosurgical generators is a switching circuit which switches energizing pulses of current from the DC power supply directly through the primary winding of the output transformer. The switching frequency establishes the frequency characteristic of the RF electrosurgical waveform. The amount of power delivered in the RF electrosurgical waveform is also related to energizing pulses switched through the primary winding. Again, the energy content of the switched energizing pulses is related to the voltage of each of those pulses and the time width, or on-time duration, of the switched energizing pulses. The responsiveness for power regulation purposes is therefore directly dependent upon the responsiveness of the switching circuitry which creates these energizing pulses.

Even though the typical electrosurgical generator will adjust the DC output voltage from the high voltage power supply according to the coagulation mode of operation selected, it is typical to require the RF amplifier and output section to perform all further regulation of the RF electrosurgical power delivered to the patient. To do so, the RF amplifier and output section primarily controls the on-time duration of the energizing pulses, for purposes of establishing output power regulation. Under very low or very high output power conditions, the time width or on-time duration of the energizing pulses may reach such small or large proportions of the overall cycle time that effective power regulation and conversion is difficult or impossible to achieve.

In both resonant circuit and switched RF amplifier output circuits, the optimum on-time for the energizing pulse is a 50% duty cycle, meaning that the on-time portion is one-half of the entire time of each cycle. As the on-time of the energizing pulses diminishes to a minimal portion of the overall cycle or as the on-time portion increases to a substantial portion of the overall cycle, the ability to regulate the output power becomes more difficult. A relatively short on-time portion of the energizing current pulse does not transfer a large amount of energy for conversion, making precise power regulation under low power delivery conditions with relatively short on-time energizing pulses more difficult. A relatively long on-time portion of the current pulse does not provide sufficient time during the off-time portion of each cycle for the energy to be converted, again making it difficult to regulate the amount of energy which is delivered under such circumstances. Thus, energizing pulses having a relatively short or a relatively long on-time do not provide the best power control and regulation capability. The optimal power regulation capability occurs when the on-time portion of each cycle of energizing pulses falls within a middle percentage of the entire cycle time.

Electrosurgical generators have typically used a type of high voltage power supply commonly known as a voltage mode DC power supply. In such a power supply, the voltage level of the supplied power is used as feedback for control and regulation purposes. A voltage mode DC power supply is relatively straightforwardly implemented by relatively inexpensive components. One of the disadvantages of a voltage mode DC high voltage power supply used in an electrosurgical generator is that it has a finite delay time when it is necessary to limit the current, or to shut down (i.e. turn off), or to rapidly ramp up, or increase, the DC output voltage. Because of the rigorous requirements for substantial variations in the RF electrosurgical power output and waveform, a voltage mode DC high voltage power supply limits the ability of the electrosurgical generator to adapt to changing tissue impedances and output power delivery and regulation circumstances.

Another type of DC power supply is commonly known as a switched current mode power supply. A current mode power supply controls the DC output voltage by controlling the amount of input current to the power supply. Because the input current can be rapidly controlled, a switched current mode power supply has the capability to respond very rapidly to changing output load conditions, and do so to a greater degree than a voltage mode DC power supply. The typical switched current mode power supply converts a source of coarsely regulated DC energy by switching pulses of input current from the coarsely regulated DC energy source through a primary winding of a conversion transformer. The energy from the pulses of input current flowing in the primary winding is transformed to the secondary winding and is then rectified. A conventional current mode controller controls the characteristics of the pulses of input current switched through the primary winding of the conversion transformer. The amount of current conducted by each pulse is sensed and fed back as a control signal to the current mode controller. The voltage of the energy converted from the conversion transformer is sensed and also fed back to the current mode controller. Based on these signals, the current mode controller generates switching signals for controlling the characteristic of pulses of input current. The current mode controller controls the time width of the pulses of input current to control the output power. The current mode controller is able to quickly adjust the pulses to increase or decrease the output voltage and the amount of power converted and transferred through the switched current mode power supply, or to cease generating the pulses altogether under extreme over-voltage or over-current conditions.

Adapting a switched current mode DC power supply to an electrosurgical generator creates difficulties not typically experienced in the typical use of a switched current mode DC to DC power supply. The leakage inductance in the conversion transformer interacts with the stray capacitance to cause the current pulses conducted through the primary winding to oscillate or "ring" at the beginning of each pulse. This ringing adversely affects the input current feedback signal and, unless suppressed, will cause the current mode controller to adjust the characteristics of the input current pulses under circumstances where no adjustment may be required or desirable, or even shut down the power conversion entirely. The typical current mode controller used in a current mode power supply has a built-in or inherent capability to suppress or "blank" an initial time portion of each input current feedback signal and thereby suppress the ringing.

However, in electrosurgical generators, the built-in blanking capability of the current mode controller is insufficient. In electrosurgical generators, electrical isolation of the generator from the conventional AC power mains is required as a safety measure, so that under a possible failure condition, electrical energy from the AC power mains does not feed through to the patient. This requires a conversion transformer having low-leakage current, typically resulting in high leakage inductance. These aspects of the conversion transformer exaggerate the ringing conditions in the input current feedback signal to the extent where the built-in blanking capability of a conventional current mode controller is not entirely satisfactory for use in a switched current mode power supply used in an electrosurgical generator.

The typical switched current mode power supply is intended for applications whose output voltage does not vary substantially as is required in electrosurgery. Additionally, blanking the initial portion of each switching signal is usually acceptable because of the relatively constant and non-varying load and power consumption conditions into which the typical current mode switched DC power supply delivers output power. However, under low output power conditions required for electrosurgical use, blanking an initial portion of an already shortened on-time of the feedback current signal may take up such a significant percentage of the feedback current signal that the remaining portion of the signal is insufficient for reliable and precise output power control and regulation.

SUMMARY OF THE INVENTION

The present invention involves an effective implementation of a switched current mode power supply as a high voltage power supply in a new and improved electrosurgical generator. Among other things, the switched current mode power supply effectively coordinates the DC output voltage supplied to an RF amplifier and output section to achieve more efficient and effective power control and regulation according to a selected mode of operation and the output power requirements of the electrosurgical generator. The DC output voltage from the current mode power supply is reduced under relatively low RF electrosurgical output power conditions so that the RF amplifier and output section are able to utilize energizing pulses having an efficient middle range of on-time in each cycle of energizing pulses delivered. The middle range of on-time percentages of each energizing pulse results in the conversion energy on an efficient and rapid basis, as well as providing more responsive RF electrosurgical output power regulation, compared to the circumstance where much wider ranges of on-time percentages are required from the RF amplifier and output section because of the relatively fixed and invariable voltage supplied by the high voltage power supply of the electrosurgical generator.

The present invention also improves the functionality of an electrosurgical generator by using a conventional current mode controller in a switched current mode DC to DC power supply in the electrosurgical generator. The current mode controller delivers a switching signal to the switching transistors of the conversion transformer at a selected one of multiple different frequencies. Under high output RF electrosurgical energy demand conditions, the current mode controller delivers the switching signals at a relatively high frequency to avoid transformer saturation, to achieve more frequent power conversion and to avoid less output power variation under high demand conditions. Under relatively low output RF electrosurgical energy demand conditions, the current mode controller delivers the switching frequency at a selected relatively lower frequency. The lower frequency extends the time width of the on-time portion of each switching signal, and thereby diminishes the relative proportion of the on-time portion which is consumed by the ringing. An extended blanking time is established for the current mode controller by external circuitry which bypasses the built-in blanking capability, thereby achieving sufficient blanking for electrosurgical use even in conjunction with a low-leakage conversion transformer. The transitions where the current mode controller changes between delivering the relatively high and low frequency switching signals is established on the basis of a hysteresis-like response characteristic. The hysteresis-like response prevents fluttering or oscillation between the multiple different frequency switching signals.

These and other features and improvements are embodied an electrosurgical generator which includes a current mode high voltage power supply that converts pulses of input current occurring at a predetermined switching frequency into a DC output voltage, and an RF amplifier and output section which receives the DC output voltage and creates an output RF electrosurgical waveform from energizing pulses having a voltage related to the DC output voltage and a time width related to a characteristic of the RF electrosurgical waveform.

Other features and improvements of the present invention are embodied in an electrosurgical generator which has a current mode high voltage power supply connected to deliver a DC output voltage to an RF amplifier and output section in response to a power supply set control signal. The set control signal is supplied by a power controller based on a selected electrosurgical mode and a selected RF electrosurgical output power. The current mode power supply creates the DC output voltage from a source of DC input energy. The current mode power supply comprises a conversion transformer having a primary winding and a secondary winding. The secondary winding is connected to deliver the DC output voltage. At least one switching transistor is connected to the primary winding to conduct pulses of input current from the source of DC input energy through the primary winding. The energy content of the pulses of current conducted through the primary winding establish the magnitude of the DC output voltage delivered from the secondary winding. A current mode controller supplies a switching signal to control the conductivity of the switching transistor. A voltage control circuit is connected to the current mode controller and responds to the DC output voltage and, the set control signal to supply a pulse control signal to the current mode controller. The current mode controller establishes an on-time duration characteristic of the switching signal in response to the pulse control signal, and the on-time duration characteristic of the switching control signal establishes a time width characteristic of each of the input pulses of current conducted by the one switching transistor through the primary winding from the source of DC input energy.

The improvements and features of the present invention also relate to a method of creating an output RF electrosurgical waveform for application in electrosurgery from a source of input DC energy. The method involves creating pulses of input current from the input DC energy source, establishing an energy content of each pulse of input current by controlling a time width of each pulse of input current, converting the energy content of the pulses of input current into a DC output voltage having a magnitude related to the energy content of the pulses of input current, creating energizing pulses having an energy content established by the DC output voltage and a time width, and converting the energy content of the energizing pulses into the output RF electrosurgical waveform.

A further improved method of the present invention involves converting DC input energy into DC output voltage used to create an output RF electrosurgical waveform having a variable power content when applied in electrosurgery. This method involves creating pulses of input current from the input DC energy, establishing an energy content of each pulse of input current by controlling a time width of each pulse of input current, converting the energy content of the pulses of input current into the DC output voltage having a magnitude related to the energy content of the pulses of input current, and regulating the time width of each pulse of input current for conversion to maintain the DC output voltage substantially constant as power of the output RF electrosurgical waveform varies.

The input current control capabilities of the current mode supply achieve the above noted significant improvements in creating and regulating the DC high voltage within an electrosurgical generator, as well as achieving better regulation and control over the RF energy and waveform delivered during electrosurgery.

A more complete appreciation of the present invention and its scope, and the manner in which it achieves the above noted improvements, can be obtained by reference to the following detailed description of presently preferred embodiments taken in connection with the accompanying drawings, which are briefly summarized below, and to the appended claims.

BRIEF DESCRIPTION OF THE DRAWINGS

FIGS. 7, 8 and 9 are waveform diagrams similar to the one shown in FIG. 6, illustrating different characteristics of the feedback current sense signal under different conditions of operation and according to the improvements of the current mode power supply shown in FIG. 4.

DETAILED DESCRIPTION

Figure 1:
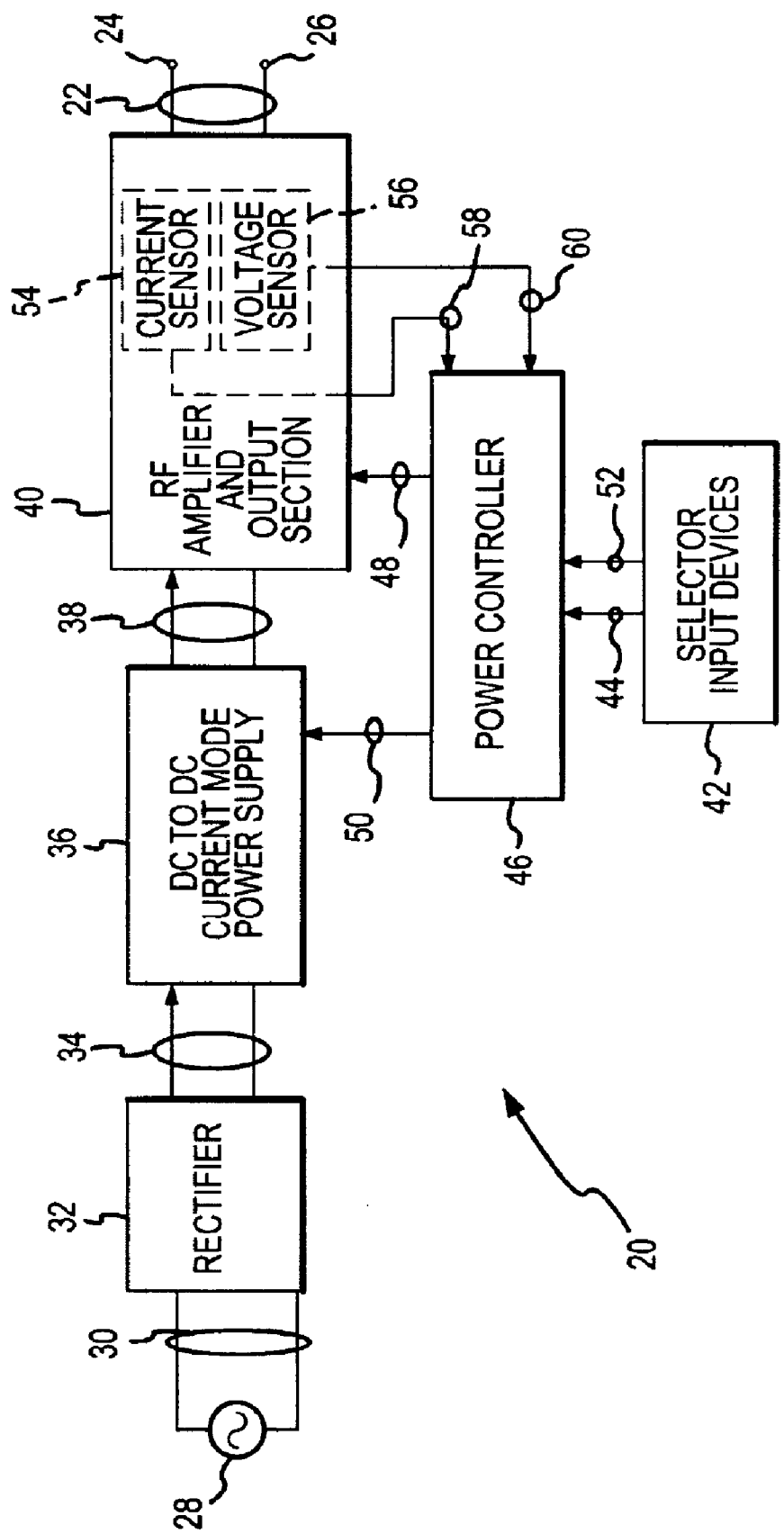
FIG. 1 is a block diagram of an electrosurgical generator incorporating the present invention.

An electrosurgical generator 20, shown in FIG. 1, creates output radio frequency (RF) electrosurgical energy which is supplied as output RF electrosurgical waveform 22 at output terminals 24 and 26. The RF electrosurgical energy from the terminals 24 and 26 is applied to the patient during electrosurgery by conventional handpieces and other instruments (not shown) connected to the terminals 24 and 26. The output RF electrosurgical energy at terminals 24 and 26 is derived from conventional alternating current (AC) electrical power at 28 supplied from conventional AC power distribution mains 30. A rectifier 32, which is connected to the AC power mains 30, converts the AC power at 28 into a relatively-coarse direct current (DC) energy or power at 34. A switched DC to DC current mode power supply 36 converts input DC power at 34 into a finely-regulated output DC energy or power at 38. The finely-regulated output DC power at 38 is supplied to an RF amplifier and output section 40. The RF output section 40 creates the RF electrosurgical waveform 22 at the terminals 24 and 26 from the output DC power at 38 supplied from the current mode power supply 36.

The characteristics of the output RF electrosurgical waveform 22 are established by selecting the mode of operation of the electrosurgical generator 20, i.e. cut, coagulation, or blend. The mode of operation is selected by the user from selector input devices 42. The power level of the output RF electrosurgical waveform 22 at the terminals 24 and 26 for the selected mode is also established by the input devices 42. Selecting the mode of electrosurgical operation and the desired output power level causes the input devices 42 to generate a plurality of output characteristic control signals 44 which are supplied to a power controller 46. In response to the output characteristic control signals 44, the power controller 46 formulates a power delivery control signal 48 which establishes the power content and waveform characteristics of the RF electrosurgical power delivered from the electrosurgical generator 20.

The power delivery control signal 48 is supplied to the RF amplifier and output section 40, and the RF amplifier and output section 40 creates the RF electrosurgical power at the terminals 24 and 26 from the output DC power at 38 supplied by the current mode power supply 36. The power controller 46 also responds to the output characteristic control signal 44 by supplying a power supply set control signal 50 to the current mode power supply 36. The current mode power supply 36 establishes desired levels of voltage and current of the DC power at 38 according to the power supply set control signal 50.

The electrosurgical generator 20 only delivers the output RF electrosurgical waveform 22 when it is activated or "keyed" to do so. The electrosurgical generator is activated by the surgeon, typically by depressing a switch attached to a handpiece or other electrosurgical instrument, or by stepping on a foot switch. Closing one of these types of activation switches causes the electrosurgical generator to deliver the output RF electrosurgical energy in the form of the waveform 22 from the terminals 24 and 26. In this regard, the input devices 42 also represent the activation switches which respond to closure by the surgeon and result in asserting an activation control signal 52. The activation control signal 52 is supplied to the power controller 46. The power controller 46 responds to the activation control signal 52 by asserting the power delivery control signal 48 to the RF amplifier and output section 40 during those times that the activation control signal 52 is asserted as a result of the surgeon activating the electrosurgical generator. The power controller 46 deasserts the power delivery control signal 48 during those times that the activation control signal 52 is not asserted when the surgeon does not activate the electrosurgical generator. In this manner, the RF amplifier and output section 40 generates the desired RF electrosurgical waveform 22 at the terminals 24 and 26 only in response to and during the time when the surgeon has activated the electrosurgical generator by asserting the activation signal 52.

The RF amplifier and output section 40 preferably includes a current sensor 54 and a voltage sensor 56. The current sensor 54 and the voltage sensor 56 detect the current and voltage, respectively, of the output RF electrosurgical energy of the waveform 22 delivered to the patient. The current and voltage sensors 54 and 56 generate output current and voltage feedback signals 58 and 60, respectively. The current and voltage feedback signals 58 and 60 are supplied to the power controller 46 so the power controller 46 can respond to the current and voltage levels of the output RF electrosurgical waveform 22 to adjust the value of the power delivery control signal 48 to establish and maintain the power of the output RF electrosurgical waveform at the level set by the user at the input devices 42 and which coordinates with the value of the power supply set control signal 50.

The improvements of the present invention reside primarily in the current mode power supply 36 and those improvements may be effectively used in an electrosurgical generator in which the other components and functionality are otherwise conventional. An improved control system for an electrosurgical generator, which may be used very effectively with the present invention, is described in the above-identified, concurrently-filed U.S. patent application. The improvements of this concurrent invention reside primarily within the power controller 46 shown in FIG. 1. In addition, the improvements of the current mode power supply 36 coordinate effectively with the two prevalent and conventional types of the RF amplifier and output section 40, shown in FIGS. 2 and 3.

Figure 2:
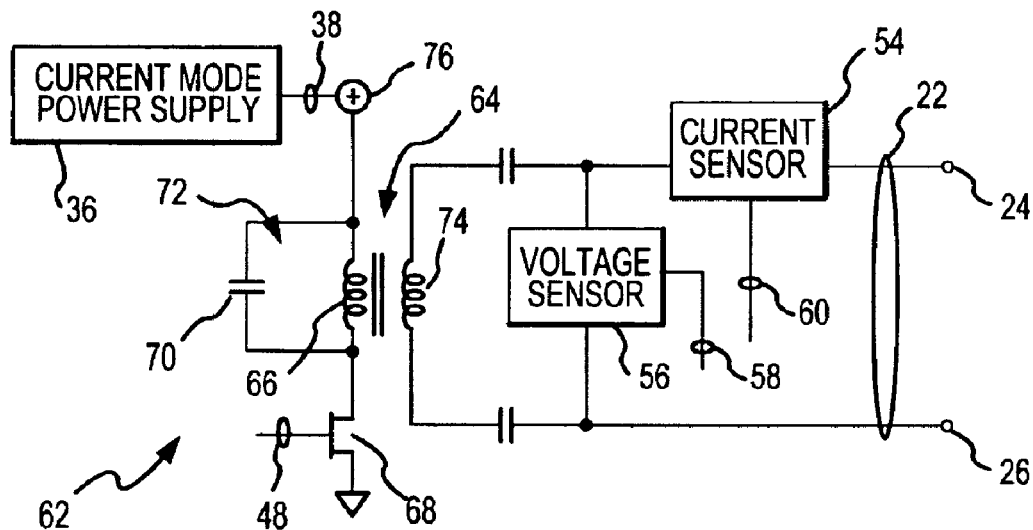
FIG. 2 is a simplified schematic diagram of a resonant circuit RF amplifier and output section which may be used in the electrosurgical generator shown in FIG. 1, with certain interactive portions of the electrosurgical generator shown in block diagram form.

One type 62 of the RF amplifier and output section 40 (FIG. 1) is shown in FIG. 2 and involves a resonant output circuit. A RF electrosurgical output transformer 64 includes a primary winding 66 through which current from the current mode power supply 36 is conducted by a driver transistor 68. A capacitor 70 is connected in parallel with the primary winding 66. The inductance of the output transformer 64 at the primary winding 66 and the capacitance of the capacitor 70 form a resonant circuit 72. An energizing pulse of current charges the resonant circuit with energy during the on-time of the driver transistor 68, established by the power delivery control signal 48. The energy from the energizing pulse causes oscillations in the resonant circuit 72, and the oscillatory current flowing in the resonant circuit 72 induces a signal which becomes the output RF electrosurgical waveform in a secondary winding 74 of the output transformer 64. The secondary winding 74 is connected to the output terminals 24 and 26, and supplies the output RF electrosurgical waveform 22 from the terminals 24 and 26. The current sensor 54 and the voltage sensor 56 sense the current and voltage of the output RF electrosurgical waveform 22 delivered from the secondary winding 74.

The waveform characteristics of the output RF electrosurgical waveform 22 are established primarily by the electrical characteristics of the oscillations within the resonant circuit 72, as modified by the effective load connected to the terminals 24 and 26. During the application of the output RF electrosurgical energy to the tissue, the primary load connected to the output terminals 24 and 26 is the impedance of the tissue through which the RF electrosurgical energy flows. The energy content of the output RF electrosurgical waveform 22 delivered from the output terminals 24 and 26 is established primarily by the energy content of the energizing pulses of current which charge the resonant circuit 72 when the driver transistor 68 is conductive. The energy content of each energizing pulse is established by a DC output voltage 76 of the output DC power 38 supplied by the current mode power supply 36 and the time width of the energizing pulse created by the driver transistor 68.

If the DC output voltage 76 from the current mode power supply is stable, the amount of energy delivered is directly related to the time width of the energizing pulse. Some conventional power controllers 46 (FIG. 1) used with electrosurgical generators assume that the DC output voltage 76 is stable and does not vary and therefore power regulation from the RF amplifier and output section 40 is accomplished as a result of adjusting the time width of the energizing pulse. To the extent that any variance does occur, it is expected that the power controller 46 (FIG. 1) will adjust the time width of the energizing pulses based on the output current and voltage feedback signals 58 and 60 (FIG. 1) to obtain the desired energy content of the output RF electrosurgical waveform 22. Such assumptions give rise to difficult or impossible conditions for effective RF output power control and regulation based on controlling only the time width of the energizing pulses. The present invention coordinates the DC output voltage 76 supplied by the current mode power supply 36 so as to permit the time width of the energizing pulses to be optimized for effective power control and regulation.

Figure 3:
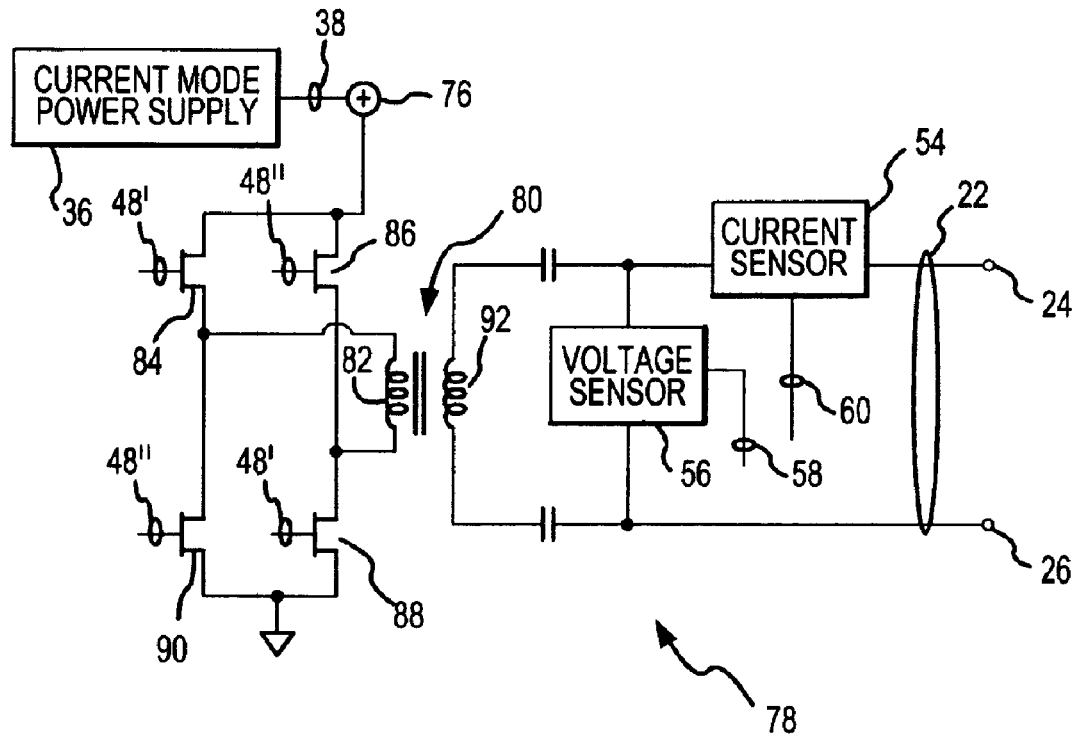
FIG. 3 is a simplified schematic diagram of a switched RF amplifier and output section which may be used in the electrosurgical generator shown in FIG. 1, as an alternative to the form of the RF amplifier and output section shown in FIG. 2, with certain interactive portions of the electrosurgical generator shown in block diagram form.

A similar situation exists in another type 78 of the RF amplifier and output section 40 (FIG. 1), shown in FIG. 3. The type 78 of RF amplifier and output section also uses an RF electrosurgical output transformer 80 having a primary winding 82 to which four driver transistors 84, 86, 88 and 90 are connected. Current from the current mode power supply 36 is conducted in one direction (downward as shown) through the primary winding 82 when the driver transistors 84 and 88 are simultaneously conductive as a result of applying a first driver power delivery control signal 48' to the transistors 84 and 88. Current is conducted in the other direction (upward as shown) through the primary winding 82 when the driver transistors 86 and 90 are simultaneously conductive as a result of applying a second driver power delivery control signal 48" to the transistors 86 and 90. The first driver power delivery control signal 48' is asserted while the second power delivery control signal 48" is not asserted, and the second driver power delivery control signal 48" is asserted while the first power delivery control signal 48' is not asserted. In this manner, current is driven through the primary winding 82 of the output transformer 80 at the RF output frequency. The alternating current flow in the primary winding is induced through the output transformer 80 to a secondary winding 92. The secondary winding is connected to the output terminals 24 and 26.

The waveform characteristics of the output RF electrosurgical waveform 22 are established primarily by the characteristics of the driver signals 48' and 48" applied to the driver transistors 84, 86, 88 and 90 which causes a corresponding current flow through the primary winding 82, as modified by the effective load connected to the terminals 24 and 26. During the application of the output RF electrosurgical energy to the tissue, the primary load connected to the output terminals 24 and 26 is the impedance of the tissue through which the RF electrosurgical energy flows. The energy content of the output RF electrosurgical waveform 22 delivered from the output terminals 24 and 26 is established primarily by the energy content of the energizing pulses of current which are conducted through the primary winding 82 by the driver transistors 84, 86, 88 and 90. The energy content of each energizing pulse is established by a DC output voltage 76 of the output DC power 38 supplied by the current mode power supply 36 and the time width of the energizing pulse created by the driver power delivery control signals 48' and 48."

Essentially the same energy delivery, regulation and control situation applies with respect to the switched type 78 of the RF amplifier and output section shown in FIG. 3, as applies to the resonant circuit type 62 of the RF amplifier and output section shown in FIG. 2. The conventional power controller 46 (FIG. 1) assumes that the DC output voltage 76 is stable and does not vary and therefore accomplishes power regulation as a result of adjusting the time width of the energizing pulse. To the extent that any variance does occur, it is expected that the output current and voltage feedback signals 58 and 60 will cause the power controller 46 (FIG. 1) to adjust the time width of the energizing pulses by adjusting the characteristics of the power delivery control signals 48, 48' and 48" applied to the driver transistors 68, 84, 86, 88 and 90. Such assumptions also give rise to similar difficult or impossible conditions for effective RF output power control. The coordination of the DC output voltage 76 supplied by the current mode power supply 36 with the time width of the driver power delivery control signals 48, 48' and 48" applied to the transistors 68, 84, 86, 88 and 90 permit the energizing pulses to be optimized for effective power control and regulation.

Figure 4:
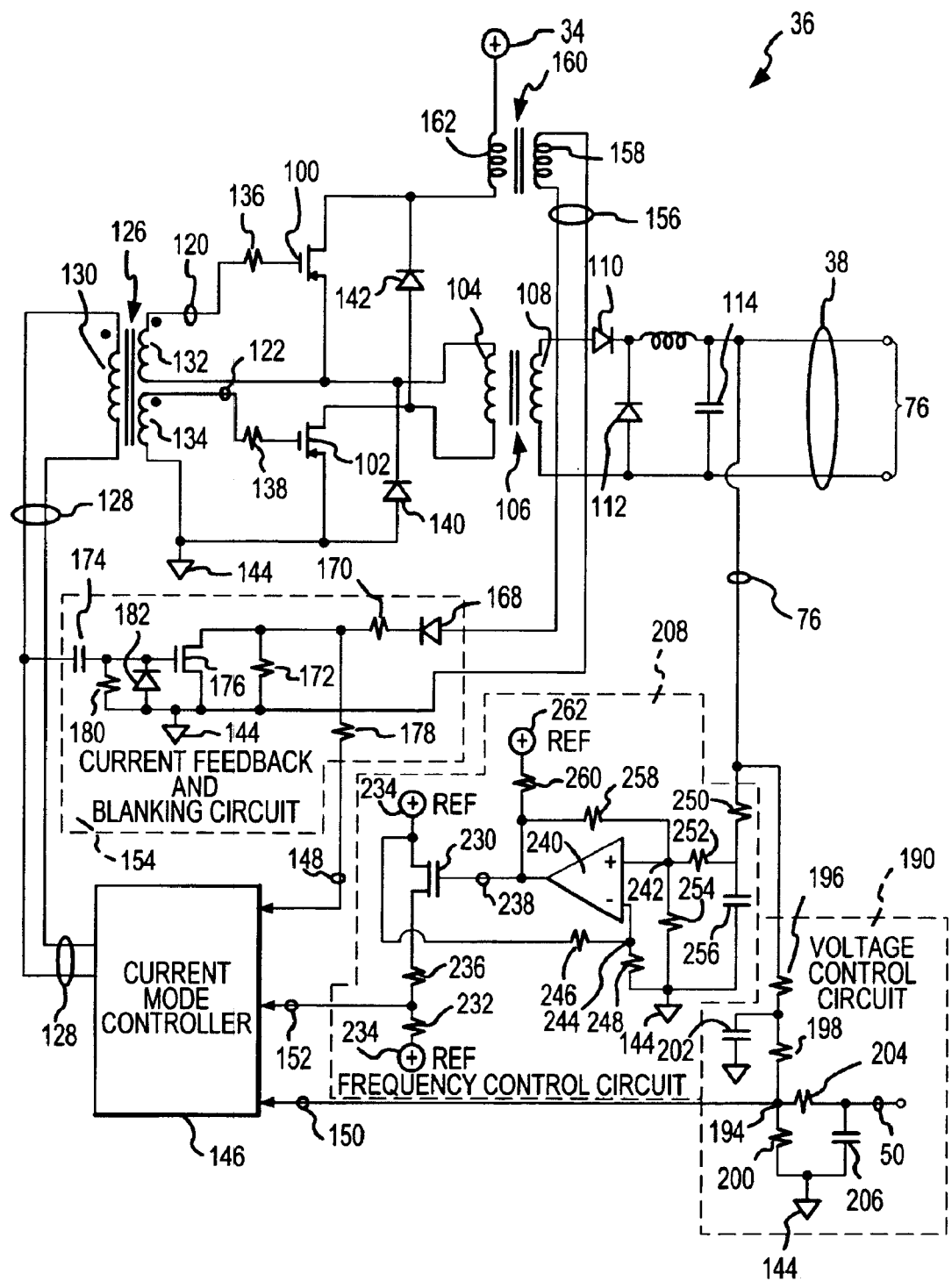
FIG. 4 is a simplified schematic and block diagram of the switched current mode power supply of the electrosurgical generator shown in FIG. 1, in which the improvements of the present invention are primarily incorporated.

The details of the improvements relating to the current mode power supply 36 are better understood by reference to FIG. 4. The current mode power supply 36 converts the coarse DC energy at 34 into the finely-regulated DC power at 38 by the action of two switching transistors 100 and 102. The transistors 100 and 102 switch pulses of input current from the DC energy at 34 through a primary winding 104 of a low-leakage, isolating, conversion transformer 106. The conversion transformer 106 effectively separates or isolates the output DC power 38 from the current mode power supply 36, which is that power supplied from the electrosurgical generator 20 (FIG. 1), from the AC electrical power 28 supplied from the AC power mains 30 (FIG. 1). This isolation assures that the AC mains power will not inadvertently feed through the electrosurgical generator to the patient or that the AC mains power will not adversely affect the electrical power delivered from the electrosurgical generator to the patient. A secondary winding 108 of the conversion transformer 106 delivers output current and voltage from the conversion transformer 106 to rectifier diodes 110 and 112 which rectified the current and supply the rectify current to a storage and filter capacitor 114. The voltage across the capacitor 114 constitutes the DC output voltage 76 from the current mode power supply 36. The current rectified by the diodes 110 and 112 and supplied by the capacitor 114 at the DC output voltage 76 across the capacitor 114 constitutes the output DC power 38 supplied by the current mode power supply 36.

Drive signals 120 and 122 are supplied to the switching transistors 100 and 102 to cause them to conduct the pulses of current through the primary winding 104 of the conversion transformer 106. The drive signals 120 and 122 are derived from a switching transformer 126. A switching signal 128 is supplied to a primary winding 130 of the switching transformer 126, and two secondary windings 132 and 134 of the transformer 126 supply the drive signals 120 and 122, respectively, in response to the switching signal 128. The drive signals 120 and 122 are supplied to gate terminals of the switching transistors 100 and 102 through resistors 136 and 138, respectively. Diodes 140 and 142 are connected relative to a reference potential 144 for the current mode power supply 36 and for the DC output voltage 76, respectively, to protect the switching transistors 100 and 102 from spurious signals created by switching current through the primary winding 104.

The drive signals 120 and 122 cause the switching transistors 100 and 102, respectively, to conduct the pulses of input current from the input DC energy at 34 through the conversion transformer 106 during an on-time of each cycle of the switching signal 128 and cause the switching transistors 100 and 102 to become nonconductive during the remaining off-time of each cycle of the switching signal 128. Each cycle of the switching signal 128 repeats at the predetermined frequency of the switching signal 128.

The amount of output DC power 38 is established by the turns ratio of the primary winding 104 and secondary winding 108 of the conversion transformer 106 and by the power content of the pulses of input current switched by the transistors 100 and 102 through the primary winding 104. The switching transistors 100 and 102 are conductive only during the on-time of each cycle of the switching signal 128. The energy content of pulses of input current conducted by the switching transistors 100 and 102 through the primary winding 104 is directly related to the on-time of the switching signal 128. Controlling the amount of on-time of the switching signal 128 directly controls the DC output voltage 76 and the amount of output DC power at 38 from the current mode power supply 36, because the turns ratio of the primary and secondary windings of the conversion transformer 106 is set and therefore not variable once the conversion transformer 106 has been manufactured.

The DC output voltage 76 and the amount of output DC power at 38 is not dependent upon the frequency of the switching signal 128. However, a relatively greater switching frequency is desired under circumstances of relatively higher demand for output DC power 38, because the higher switching frequency replenishes the power in the filter capacitor 114 on a more frequent basis to maintain the DC output voltage 76 more uniform with less variations under higher power demand conditions. The higher switching frequency also has the effect of avoiding saturation of the transformer, thereby permitting more effective cower control. Under conditions of relatively lower demand for output DC power, a relatively lesser switching frequency is not a detriment because the relatively lower power demand causes less variation in the DC output voltage 76 across the filter capacitor 114.

A conventional current mode controller 146 for the switched current mode power supply 36 establishes the characteristics of the switching signal 128, and as a result, the amount of output DC power supplied at 38 by the current mode power supply 36. The switching signal 128 controls the characteristics of the drive signals 120 and 122 which determine the conductivity characteristics of the switching transistors 100 and 102. The on-time and off-time characteristics of the switching signal 128 establishes the on-time of each pulse of current conducted through the primary winding 104 of the conversion transformer 106. The frequency characteristic of the switching signal 128 sets the frequency at which the pulses of input current are conducted through the primary winding 104 of the conversion transformer 106. The current mode controller 146 responds to a feedback current sense signal 148, a pulse width control signal 150 and a frequency control signal 152 to establish the characteristics of the switching signal 128.

The feedback current sense signal 148 is supplied by a current feedback and blanking circuit 154. The feedback current sense signal 148 is derived from an input current sense signal 156 which is supplied from a secondary winding 158 of a current sense transformer 160. A primary winding 162 of the current sense transformer 160 is connected between the source 34 of input DC energy and the switching transistor 100. The input current pulses conducted through the primary winding 104 by the switching transistors 100 and 102 also flow through the primary winding 162 of the current sense transformer 160. The input current sense signal 156 is thus derived from and directly related to the amount of current switched through the primary winding 104 of the conversion transformer 106.

Figure 5:
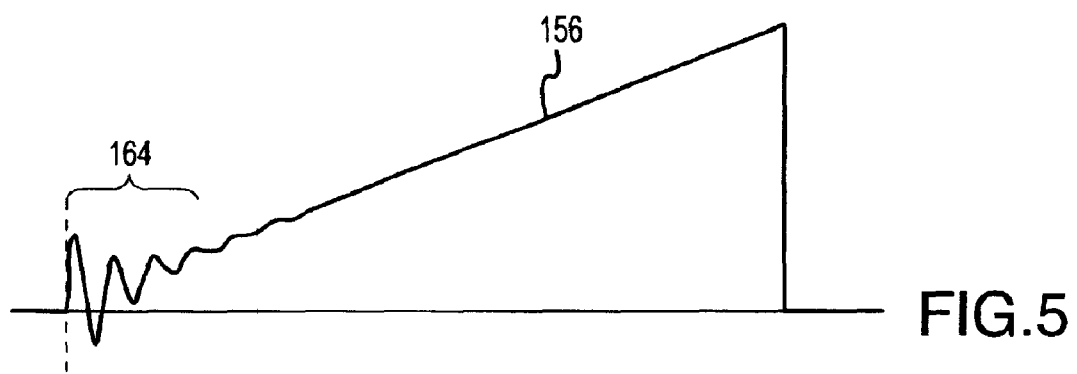
FIG. 5 is a waveform diagram illustrating an input current sense signal generated from the current mode power supply shown in FIG. 4.

The feedback current sense signal 148 is derived from the input current sense signal 156. The feedback and blanking circuit 154 modifies the input current sense signal 156 to blank out or eliminate an initial portion 164 of the input current sense signal 156 shown in FIG. 5, and thereby create the feedback current sense signal 148 shown in FIG. 6. As is typical of a switched current mode power supply, the initial portion 164 of the input current sense signal 156 (FIG. 5) is made up of oscillations or ringing which are caused by an inherent resonant circuit resulting from the leakage capacitance and the inductance of the conversion transformer 106 (FIG. 4). The ringing results from the stimulation of this resonant circuit by each pulse of input current conducted through the primary winding 104 by the switching transistors 100 and 102. If not blanked or suppressed, the ringing portion 164 (FIG. 5) will be interpreted by the current mode controller 146 (FIG. 4) as an input current related signal, and the current mode controller 146 will respond by modifying or changing the characteristics of the switching signal 128 or by terminating the delivery of the switching signal 128 because the ringing will be interpreted as an excessive current delivery condition. Blanking the ringing portion 164 of the input current sense signal 156 prevents the current mode controller 146 from responding inappropriately or shutting down the current mode power supply 36.

Most conventional current mode controllers have a conventional built-in capability to blank out a predetermined time of an input current sense signal (e.g. 156). However, the low leakage current characteristics of the isolating conversion transformer 106 emphasizes and extends the ringing portion 164 (FIG. 5) to such an extent that the usual blanking capability of a conventional current mode controller is insufficient to suppress the unwanted and anomalous ringing in a current mode power supply having the isolation capability necessary for an electrosurgical generator. The built-in blanking capabilities of the current mode controller 146 are bypassed by using the external feedback and blanking circuit 154 to create a blanking interval 166 of the feedback current sense signal 148 (FIG. 6) of a longer and sufficient time duration for eliminating a significant portion or all of the ringing portion 164 (FIG. 5) of the input current sense signal 156. Not all of the ringing portion 164 (see FIG. 6) need be completely removed by the blanking interval 166, but a substantial amount of the ringing is suppressed or blanked to enable the current mode controller 146 to be used effectively as a high-voltage power supply in an electrosurgical generator.

Figure 6:
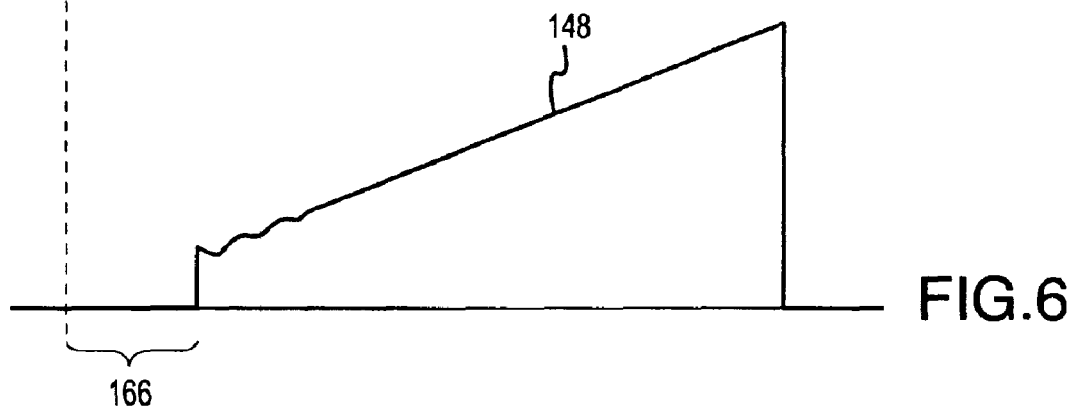
FIG. 6 is a waveform diagram illustrating a feedback current sense signal blanking an initial portion of the input current sense signal shown in FIG. 5.

The ringing portion 164 of the input current sense signal 156 (FIG. 5) is eliminated by the current feedback and blanking circuit 154 (FIG. 4) as a result of driving the ringing portion 164 of the input current sense signal 156 (FIG. 5) to a zero value during the blanking interval 166 (FIG. 6). With reference to FIG. 4, the pulses of current flowing through the primary winding 162 induce the input current sense signal 156 from the secondary winding 158. A diode 168 rectifies the input current sense signal 156 and applies the rectified input current sense signal 156 to two resistors 170 and 172. The resistor 170 is connected between the diode 168 and a transistor 176. Simultaneously with the delivery of the input current sense signal 156, the on-time portion of the switching signal 128 is applied through a capacitor 174 to the gate terminal of the transistor 176, causing the transistor 176 to become conductive. The conductive transistor 176 effectively drives the value of the rectified input current sense signal 156 conducted through the resistor 170 to reference potential 144. The value of the feedback current sense signal 148 is likewise driven to zero, because the feedback current sense signal 148 is derived from the signal applied through the resistors 170 and 178 to the current mode controller 146.

The time period during which the transistor 176 is conductive corresponds to the time period 166 (FIG. 6) during which the initial portion 164 (FIG. 5) of the input current sense signal 156 is blanked. This blanking time period is established by the values of a resistor 180 and the capacitor 174, which together form a time delay circuit. The values for the resistor 180 and the capacitor 174 are selected so that their RC time constant results in a blanking time period 166 (FIG. 6) of sufficient time duration to eliminate the ringing portion 164 (FIG. 5) of the input current sense signal 156 that results from the use of a low-leakage, conversion transformer 106 in the current mode power supply 36. A diode 182 protects the transistor 176 from anomalous voltages that may occur from the primary winding 130 of the switching transformer 126.

A voltage control circuit 190 supplies the pulse width control signal 150 to the current mode controller 146, and the current mode controller responds to pulse width control signal 150 to establish the on-time characteristics of each cycle of the switching signal 128. The magnitude of the pulse control signal 150 varies in relation to that magnitude of the DC output voltage 76 which is fed back to the voltage control circuit 190. The power supply set control signal 50 is established by the power controller 46 (FIG. 1) based on the selected mode of electrosurgical operation (cut, coagulation or blend) and the amount of output power selected for performing the electrosurgical procedure in that mode of operation. In general, the magnitude of the set control signal 50 varies inversely to the amount of DC output voltage or power requested for a selected mode of operation. For example, at maximum output power, the value of the set signal 50 is zero, and for the minimum output power, the value of the set signal 50 is a predetermined maximum level which correlates with a predetermined percentage of the value of the maximum DC output voltage 76.

The set signal 50 controls and establishes the magnitude of the DC output voltage 76 from the current mode power supply 36. To the extent that the DC output voltage 76 varies from the desired level of DC output voltage established by the set signal 50, the voltage control circuit 190 supplies the pulse control signal 150 having a value which represents the difference between the actual DC output voltage 76 and the desired DC output voltage represented by the set signal 50. The current mode controller 146 responds to changes in the pulse control signal 150 by adjusting the width of the on-time of each cycle of the switching signal 128. The adjustments in the width of the on-time of each cycle of the switching signal 128 cause changes in the amount of input DC energy at 34 converted to result in the desired amount of DC output voltage 76 established by the set signal 50.

In addition, the voltage control circuit 190 varies the value of the pulse control signal 150 so that the current mode controller 146 creates the on-time portion of each cycle of the switching signal 128 at approximately the middle percentage range of the total time duration of each cycle of the switching signal 128. Preferably, the pulse width control signal 150 will cause the current mode controller 146 to supply a switching signal 128 that has approximately a 50% on-time. By causing the on-time portion to be approximately in the middle percentage range of the entire cycle duration, the switching signal 128 creates optimal responsiveness and efficiency in the power conversion and regulation achieved by the current mode power supply 36.

An example of the manner in which the voltage control circuit 190 operates is illustrated by the circumstance where the DC output voltage 38 is less than the desired value established by the set control signal 50. Under such circumstances, an increase in the on-time of each cycle of the switching signal 128 is necessary to cause more input DC energy to be converted to increase the magnitude of the DC output voltage 76. As the DC output voltage increases because of the increased on-time width of the switching signal 128, the DC output voltage 76 begins to rise to a level which is commensurate with the desired output voltage established by the set control signal 50. Under those circumstances, the difference between the DC output voltage 76 and the value represented by the set control signal 50 diminishes, causing the pulse control signal 150 to decrease. This functionality continues until the width of the on-time of the switching signal 128 has been adjusted by the current mode controller 146 to provide the desired DC output voltage 76 at the level which correlates with the set signal 50. This example of functionality also applies in the opposite manner under circumstances where the DC output voltage 76 increases above the level which corresponds to the set signal 50.

Because the value of the set control signal 50 is coordinated with a DC output voltage 76 that should normally be achieved by a middle range of on-time from each cycle of the switching signal 128, the pulse control signal 150 will ultimately settle at a value which results in the middle range, preferably 50%, of on-time and each cycle of the switching signal 128. The pulse control signal 150 will assume approximately the same value with each different set control signal 150, once the current mode power supply 36 has achieved regulation stability, because of the coordinated relationship between the value of the set control signal 50 and the desired value of DC output voltage 76.

Conventional current mode controllers have a built-in voltage control feature which responds to the output voltage of the current mode power supply with which the current mode controller is used. When a relatively low amount of power is drawn from the current mode power supply, the built-in voltage control feature of the conventional current mode controller causes the current mode controller to enter a standby state. The standby state is achieved as a result of the current mode controller decreasing the on-time of each cycle of the switching signal to a minimal time width to maintain the DC at output voltage. Upon sensing a greater demand for output DC power, as reflected by a diminished DC output voltage, the current mode controller increases the on-time of each cycle of the switching signal to increase the DC output voltage.

For electrosurgery, it is necessary to maintain the DC output voltage 76 at the value established by the set control signal 50 even during times when the RF amplifier and output section 40 (FIG. 1) is not drawing power from the current mode power supply 36. In electrosurgery, it is typical that there are relatively numerous relatively short time intervals when the RF electrosurgical energy is delivered to the tissue, interspersed with an equal number of relatively short periods where the RF electrosurgical energy is not delivered. Thus, permitting the current mode controller 146 to enter a standby state is not acceptable for electrosurgical use, because there will be some delay upon transitioning out of that low-power standby state into a high-power delivery state.

The voltage-control circuit 190 generates the pulse control signal 150 by summing or adding a proportional value of the DC output voltage 76 with a proportional value of the set control signal 50 at a summing junction or node 194. The contribution to the pulse control signal 150 at the node 194 from the DC output voltage 76 is established by a voltage divider circuit comprising resistors 196, 198, 200, and 204. A capacitor 202 is connected between the resistors 196 and 198 to filter the high frequency voltage contribution at node 194 from the DC output voltage 76. The contribution to the pulse control signal 150 from the set control signal 50 at the node 194 is also established by a voltage divider network which comprises resistors 204 and 200. A capacitor 206 is connected in parallel with the resistors 204 and 200 to stabilize the value of the set control signal 50.

The voltage contribution at the node 194 from the set control signal 50 is established by the value of the set control signal 50 from the Dower controller 46 (FIG. 1) depending upon the selected mode of electrosurgical operation and the desired output power. The voltage contribution from the set control signal 50 is inverted relative to the voltage contribution at the node 194 from the DC output voltage 76. This relative inversion of values causes the magnitude of the pulse control signal 150 to attempt to obtain a constant value which is approximately constant without regard to the level of the DC output voltage 76 and which results in the on-time width of each cycle of the switching signal 128 being in a middle percentage range. Consequently, the DC output voltage 38 from the current mode power supply 36 is regulated with middle range of on-times of each cycle of the switching signal 128 to supply the output DC power 76 set by the set control signal 50.

The frequency characteristic of the switching signal 128 is established by the frequency control signal 152, which is applied to the current mode controller 146 by a frequency control circuit 208. The current mode controller 146 establishes the frequency of the switching signal 128 at a relatively high rate or at a relatively low rate in response to the frequency control signal 152. The frequency at which the current pulses are conducted through the conversion transformer is directly related to the frequency of the switching signal 128, because the switching signal 128 creates the drive signals 120 and 122 which switch the pulses of input current through the conversion transformer 106. As discussed above, the output power delivery from the current mode power supply 36 is not dependent upon the frequency at which the pulses of current are switches through the conversion transformer 106. However, the improvement of changing the frequency of the switching signal 128, and hence the frequency of conducting input current pulses through the conversion transformer, is that better power control and regulation is available from the current mode power supply 36 under relatively low output voltage and power demand conditions.

Under low output power conditions, the on-time width of each cycle of the switching signal 128 is reduced compared to the on-time width of each cycle of the switching signal 128 under relatively high output power conditions, under conditions where the frequency of the switching signal 128 remains unchanged. The reduced on-time width under low output power conditions causes in the ringing portion 164 of the input current sense signal 156 (FIG. 5) to consume a relatively large portion of the entire duration of the on-time width. Thus, the feedback current sense signal 148 with the blanked portion 166 (FIG. 6) is of smaller proportion to the overall on-time width, thereby making regulation of the output power more difficult under low power demand conditions. This situation is illustrated in FIGS. 7 and 8.

Waveform 210, shown in FIG. 7, illustrates the feedback current sense signal 148 which occurs under relatively high output DC power demand conditions. The waveform 210 also illustrates the frequency of the switching signal 128 (FIG. 4) under such high output DC power demand conditions, because the switching signal 128 creates the input current sense signal 156 (FIG. 4) from which the feedback current sense signal 148 is derived. As shown in FIG. 7, on-time portion 212 of each cycle 214 of waveform 210 is approximately 50% of the entire time width of each cycle, and the blanked portion 166 consumes approximately one fourth of the on-time portion 212. Under relatively low output power demand conditions, the on-time portion 212 of each cycle 214 of the switching signal 128 (FIG. 4) is reduced, for example, to approximately 25% of each cycle as illustrated by the waveform 216 shown in FIG. 8. At this 25% on-time, a considerably larger amount of the on-time portion 212 of the feedback current sense signal 148 is consumed by the blanked portion 166. As discussed above, the blanked portion 166 is established by the time constant of the resistor 180 and the capacitor 174 (FIG. 4), making the blanked portion 166 constant in time width. As shown in FIG. 8, the blanked portion 166 may consume over one-half of the on-time width 212 of the of the feedback current sense signal 148. The blanked portion 166 of the waveform 216 becomes significant enough to reduce the feedback current sense signal 148 to a width that is so short that the current mode controller 146 (FIG. 4) experiences a diminished capability for reliably and precisely controlling the DC output voltage of the current mode power supply.

On the other hand, if the frequency of the switching signal 128 (FIG. 4) is reduced as shown in FIG. 9 to one-fourth of the frequency shown in FIGS. 7 and 8, the on-time portion 212 of the resulting waveform 218 shown in FIG. 9 consumes a greater duration of the on-time portion 212 of the current sense signal 148. The blanked portion 166 of the waveform 218 consumes a considerably smaller relative portion of the on-time portion 212 when the frequency is reduced. Under the circumstances shown in FIG. 9, the feedback current sense signal 148 becomes more responsive to the current mode controller 146 (FIG. 4) for controlling the DC output voltage, because the relatively smaller blanked portion 166 of the on-time duration 212 constitutes a more responsive signal for use by the current mode controller 146 (FIG. 4).

Elongating the cycle duration 214 of the feedback current sense signal 148 by reducing the frequency of the switching signal 128 (FIG. 4), as shown by comparing FIGS. 8 and 9, has the effect of stretching the on-time portion 212 of the feedback current sense signal 148 and diminishing the amount of the on-time portion 212 which is consumed by the blanking portion 166. As a consequence, the longer on-time portion of the lower frequency establishes a more precise input current sense signal 148 for use by the current mode controller 146 (FIG. 4) for regulating the output DC power from the current mode power supply. Changing the frequency of the switching signal 128 (FIG. 4) to a relatively lower frequency under relatively low output voltage conditions thereby establishes a more precise basis for regulating and controlling the DC output voltage 76 from the current mode power supply 36 (FIG. 4). Changing the frequency has no effect on the amount of output voltage delivered by the current mode power supply 36, since the output voltage is not dependent on the frequency, as discussed above. However, control and regulation is dependent upon the on-time width of the switching signal 128 (FIG. 4), and that on-time width becomes more precise for regulating the DC output voltage delivered under relatively low electrosurgical output voltage conditions.

The frequency control signal 152 generated by the frequency control circuit 208 causes the current mode controller 146 to change the frequency of the switching signal 128, as understood by reference to FIG. 4. The frequency control circuit 208 causes the frequency control signal 152 to vary in relation to the DC output voltage 76. The DC output voltage 76 is established by the set control signal 50, as described above in conjunction with the voltage control circuit 190. Consequently, the frequency control signal 152 is indirectly related to the value of the set control signal 50.

The frequency control circuit 208 establishes the value of the frequency control signal 152 at a relatively lower value which causes the current mode controller 146 to set the frequency of the switching signal 128 at a relatively lower rate when a relatively low DC output voltage 76 is delivered, based on the set control signal 50. The frequency control circuit 208 establishes the value of the frequency control signal 152 at a relatively higher value which causes the current mode controller 146 to set the frequency of the switching signal 128 at a relatively higher rate when a relatively high DC output voltage 76 is delivered, based on the set control signal 50. Moreover, the frequency control circuit 208 also transitions the frequency control signal 152 between the relatively higher and relatively lower values on the basis of a hysteresis-like response curve 220, shown in FIG. 10, in such a way that the frequency of the switching signal 128 transitions from the relatively low rate to the relatively high rate at a relatively greater DC output voltage than the DC output voltage at which the frequency of the switching signal 128 transitions from the relatively high rate to the relatively low rate.

Figure 10:
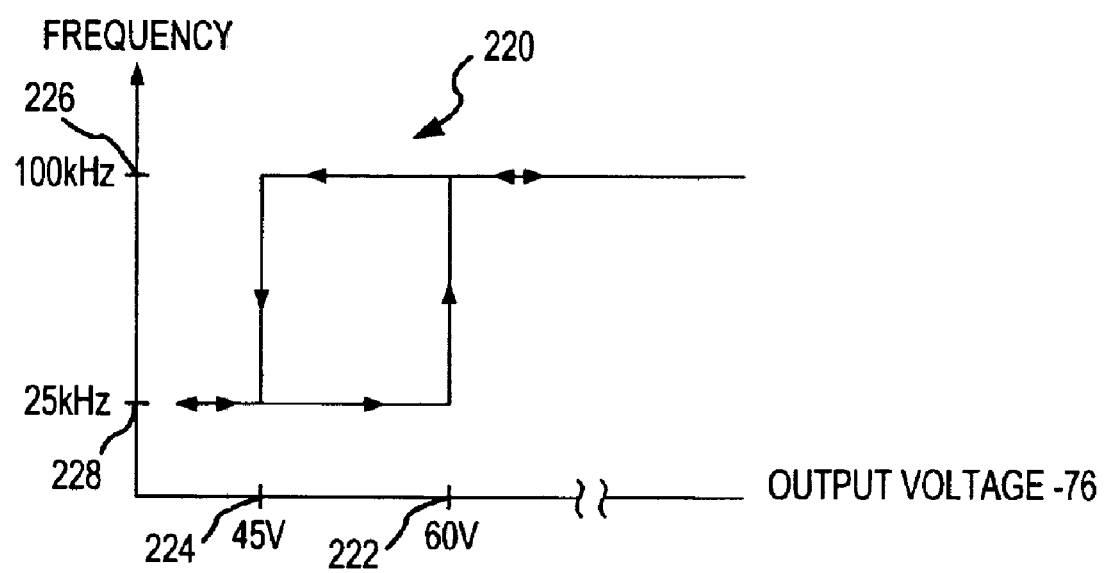
FIG. 10 is a graph of frequency of a switching signal used by the current mode power supply shown in FIG. 4 versus the output voltage generated from the current mode power supply shown in FIG. 4, illustrating a hysteresis-like response characteristic created by a frequency control circuit of the current mode power supply shown in FIG. 4.

As shown in FIG. 10 by the hysteresis-like response curve 220, the DC output voltage 76 diminishes from a relatively higher value above point 222 (e.g. 60 volts) to a relatively lower value at point 224 (e.g. 45 volts), the frequency of the switching signal 128 changes from the higher rate shown at point 226 (e.g. 100 kHz) to the lower rate shown at point 228 (e.g. 25 kHz) at the transitional voltage 224 (e.g. 45 volts). Under conditions where the DC output voltage 76 increases from a low value less than point 224 to a relatively higher value at point 222, the frequency of the switching signal 128 changes from the lower rate shown at 228 to the higher rate shown at 226 at a transitional voltage 222 (e.g. 60 volts). The frequency of the switching signal 128 will stay at the relatively low rate shown at 228 when the output voltage is increasing from the point 224 to the point 222, and then will transition to the relatively high rate shown at 226 once the output voltage reaches the level shown at point 222. The frequency of the switching signal 128 will stay at the relatively higher rate shown at 226 when the output voltage is decreasing from the point 222 to the point 224, and then will transition to the relatively lower rate shown at 228 once the output voltage falls the level shown at point 224.

By changing from the high switching frequency to the low switching frequency at a lower voltage 224 than the voltage 222, and by changing from the low switching frequency to the high switching frequency at a higher voltage 222 than the voltage 224, oscillation or fluttering between the two switching frequencies is avoided as might otherwise occur if the frequency change occurred at a single predetermined output voltage where the electrosurgical generator happened to be operating. Consequently, once a change occurs at point 224 from the relatively high frequency 226 to the relatively low frequency 228, or once a change occurs at point 222 from the relatively low frequency 228 to the relatively high frequency 226, the frequency should not change again until the DC output voltage 76 changes substantially. Of course, because of the output voltage regulation capability of the voltage control circuit 190 in relation to the set control signal 50, such changes should not occur during normal use of the electrosurgical generator except in connection with changes in the selected mode or output power. Accordingly, the pulse current switching frequency of the current mode power supply 36 should remain relatively unchanged once the set control signal 50 is established according to the selected mode and output power. The hysteresis-like response characteristic 220 (FIG. 10) of the frequency control circuit 208 thereby permits small changes in the DC output voltage as would occur from normal regulation without causing the frequency of the switching signals to oscillate or flutter between different frequencies.

The frequency control circuit 208 shown in FIG. 4 changes the frequency control signal 152 depending on the level of the DC output voltage 76 according to the hysteresis-like response exemplified by the curve 220 (FIG. 10). The current mode controller 146 establishes the frequency of the switching signal 128 at a relatively low rate when the level of the frequency control signal 152 is relatively lower and establishes a relatively high frequency of the switching signal 128 when the level of the frequency control signal 152 is relatively higher. In this regard, the frequency control signal 152 may be regarded as digital in nature because of the high-frequency or low-frequency response of the current mode controller 146. The current mode controller 146 has conventional internal captive circuitry to establish the threshold at which the level of the frequency control signal 152 is regarded as relatively lower or relatively higher for purposes of changing the frequency of the switching signal 128.

A transistor 230 of the frequency control circuit 208 controls whether the frequency control signal 152 is higher or lower. When the transistor 230 is nonconductive, the frequency control signal 152 is at the relatively lower level because it is connected through a resistor 232 to the a reference potential 234 of the current mode controller 36. On the other hand, when the transistor 230 is conductive, voltage from the reference potential 234 is applied through the conductive transistor 230 to a junction of resistors 236 and 232. The signal at the junction between resistors 236 and 232 is elevated to the higher level as a result of current flow conducted by the transistor 230 through the resistor 236, which supplements the current flow from the reference potential 234 through the resistor 232 and changes the conventional capacitive input of the current mode controller 146 more rapidly. The signal level at the junction between resistors 236 and 232 constitutes the frequency control signal 152.

The transistor 230 is rendered conductive and nonconductive by an output signal 238 from a comparator 240. When the output signal 238 from the comparator 240 is at a relatively high value, the transistor 230 is conductive. When the output signal 238 from the comparator 240 is at a relatively low value, at the level of the reference potential 144, the transistor 230 is nonconductive. The output signal 238 from the comparator 240 is controlled by the relative values of signals applied at nodes 242 and 244 to the positive and negative input terminals, respectively, of the comparator 240.

The signal applied from the node 244 connected to the negative input terminal of the comparator 240 establishes the reference value which causes the comparator 240 to switch the output signal 238 between the high and low output states. Voltage of the reference 234 is applied through a voltage divider formed by resistors 246 and 248. The voltage at the node 244 at the junction between resistors 246 and 248 is a proportional amount of the voltage from the reference 234. Because the voltage from the reference 234 is constant, the voltage at the negative input terminal from node 244 is also constant.

The signal applied from the node 242 to the positive input terminal of the comparator 240 is dependent upon the DC output voltage 76. Changes in the DC output voltage 76 cause the comparator 240 to change the states of its output signal 238. The DC output voltage 76 is applied to a voltage divider formed by the series-connected resistors 250, 252 and 254. A capacitor 256 is connected at the junction of resistors 250 and 252 to filter and stabilize the value of the signal at the node 242. Because of the voltage dividing effect of the series connected resistors 250, 252 and 254, the voltage at the node 242 is directly related to the value of the DC output voltage 76. However, the relationship of the DC output voltage 76 to the voltage at the node 242 is not linear because of a resistor 258. The resistor 258, in combination with the comparator 240, creates the hysteresis-like response 220 (FIG. 10) of the frequency control circuit 208.

The hysteresis-creating resistor 258 is connected in series with a resistor 260 and the resistor 254. The series connection of resistors 260, 258 and 254 extends between a reference voltage source 262 and the reference potential 144 of the current mode power supply 36. Because the resistor 258 is connected to the node 242, the resistor 258 influences the voltage at the node 254 created by the voltage-dividing effect of the resistors 260, 258, and 254.

When the output signal 238 from the comparator 240 is at the relatively high level, that level is comparable to the voltage of the reference 262. Under those circumstances, the connection of the resistor 258 to a relatively high voltage level causes the voltage at the node 242 to be elevated above the value which would exist only because of the voltage-dividing effect of the resistors 260, 258 and 254. As a result, the voltage from the node 242 at the positive input terminal of the comparator 240 is elevated over the value which would normally be established by the effect of the voltage divider resistors 260, 258 and 254. With the elevated voltage contribution from the resistor 258 at the node 242, the DC output voltage 76 must decrease to a lower level in order to decrease the voltage at node 242 below the voltage at node 244 to cause the comparator 240 to change the output signal 238 from the relatively high level to the relatively low level. The voltage contribution from the resistor 258 causes the node 242 to remain at a higher voltage level longer than would otherwise occur because of a decrease in the DC output voltage 76, and it is this effect which creates the hysteresis that results in the frequency of the switching signal 128 remaining at the high rate 226 as the DC output voltage 76 decreases from the voltage at 222 to the voltage at 224, as shown in FIG. 10.

On the other hand, when the output signal 238 from the comparator 240 is at the relatively low level, the junction between resistors 258 and 260 is essentially at reference potential 144. Under those circumstances, the resistor 258 is essentially connected in parallel with the resistor 254, thereby reducing the effective value of the resistor 254 in the voltage divider circuit established by resistors 260, 258 and 254. With a lower effective value of the resistor 254 in the voltage divider circuit, caused by the effective parallel connection of the resistors 258 and 254, the DC output voltage 76 must rise to a higher level to elevate the voltage at the node 242 above the voltage at the node 244 and cause the comparator 240 to change the output signal 238 from the low level to the relatively high level. The added resistance from the resistor 258 causes the node 242 to remain at a lower voltage level longer than would otherwise occur because of an increase in the DC output voltage 76, and it is this effect which results in the frequency of the switching signal 128 remaining at the low rate as the DC output voltage 76 increases. This effect is illustrated in the hysteresis-like curve 220 shown in FIG. 10, where the DC output voltage must increase from point 224 to point 222 before the switching frequency increases from the relatively low rate at 228 to the relatively high rate at 226.

In essence, the level of the output signal 238 from the comparator 240 has the effect of connecting the hysteresis-creating resistor 258 in a circuit relationship with the input terminal at node 242 to require greater excursions in the DC output voltage 76 to change states of the comparator 240, depending on the existing state of the comparator. This creates the hysteresis-like effect shown by curve 220 (FIG. 10), because the high and low frequencies of the switching signal 128 are caused by and correspond to the high and low levels of the output signal 238 from the comparator 240.

The current mode power supply 36 has the advantage of being able to generate a DC power voltage 76 at multiple different levels that are coordinated with the selected mode of electrosurgical operation and the selected amount of RF electrosurgical power to be delivered, by using a conventional current mode controller 146 (FIG. 4). The DC output voltage 76 is set to the different voltage levels to establish an on-time portion of the switching signal which is approximately in a middle percentage range of the total time duration of each cycle of the switching signal. Establishing the on-time portion of each cycle of the switching signal in the middle percentage range provides optimal regulation and control efficiency for regulating the DC output voltage 76 at the desired level commensurate with the mode and power selected. The frequency of the switching signal 128 is changed to shorten and lengthen the on-time portion of each cycle of the switching signal 128 to diminish the undesirable and anomalous effects of ringing which is inherent in the input current sense signal 156 of a current mode power supply. The blanking function of the feedback and blanking circuit 154, which is external to the current mode controller 146, enables the use of a conventional current mode controller 146 in connection with a low-leakage, tightly-coupled, isolating conversion transformer 106 as is desired for use in an electrosurgical generator. The hysteresis-like response to changing the frequency of the switching signal, caused by the frequency control circuit 208, permits the current mode power supply to change switching frequencies relative to the amount of output power delivered, to again enhance the control and regulation of the DC output voltage at a level which is optimal according to the selected mode and power for use by the RF amplifier and output section 40 of the electrosurgical generator 20. Many other advantages will be apparent after gaining a complete understanding of the nature and improvements of the present invention.

Presently preferred embodiments of the invention and its improvements have been described with a degree of particularity. This description has been made by way of preferred example. It should be understood that the scope of the invention is defined by the following claims, which should not be unnecessarily limited by the detailed description of the preferred embodiments set forth above.

What is claimed is:

1. An electrosurgical generator, comprising:

a current mode power supply operative to convert pulses of input current occurring at a predetermined switching frequency into a DC output voltage;

an RF amplifier and output section receptive of the DC output voltage and operative to create an output RF electrosurgical waveform from energizing pulses having a voltage related to the DC output voltage and a time width related to a characteristic of the RF electrosurgical waveform; and wherein:

the current mode power supply includes a current mode controller for supplying a switching signal to define and control the pulses of input current and a frequency control circuit external of and connected to the current mode controller;

the frequency control circuit responding to the DC output voltage to supply a frequency control signal to the current mode controller, the frequency control circuit supplying and maintaining the frequency control signal at a first value in response to a relatively higher value of the DC output voltage, the frequency control circuit also supplying and maintaining the frequency control signal at a second value in response to a relatively lower value of the DC output voltage; and the current mode controller responding to the frequency control signal to maintain the switching signal at a predetermined higher rate in response to and for the duration of the first value of the frequency control signal and to maintain the switching signal at a predetermined lower rate in response to and for the duration of the second value of the frequency control signal.

2. An electrosurgical generator as defined in claim 1, wherein:

the frequency control circuit changes the frequency control signal from the second value to the first value in response to the DC output voltage increasing to a first predetermined DC output voltage from a voltage less than the first predetermined DC output voltage;

the frequency control circuit changes the frequency control signal from the first value to the second value in response to the DC output voltage decreasing to a second predetermined DC output voltage from a voltage greater than the second predetermined DC output voltage; and the first predetermined DC output voltage is greater than the second predetermined DC output voltage.

3. An electrosurgical generator as defined in claim 1, wherein:

the frequency control circuit includes a hysteresis-creating circuit element and a comparator connected to a hysteresis-creating circuit element and responsive to the DC output voltage, the comparator connecting the hysteresis-circuit element in one circuit relationship to establish the first value of the frequency control signal in response to the DC output voltage increasing to the first predetermined DC output voltage from a voltage less than the first predetermined DC output voltage, and the comparator connecting the hysteresis-circuit element in another circuit relationship to establish the second value of the frequency control signal in response to the DC output voltage decreasing to the second predetermined DC output voltage from a voltage greater than the second predetermined DC output voltage.

4. An electrosurgical generator as defined in claim 1, further comprising:

a power controller operative to deliver a plurality of different set control signals for each of a plurality of different electrosurgical modes of operation of the electrosurgical generator; and wherein:

the current mode power supply further includes a voltage control circuit connected to the current mode controller, the voltage control circuit receiving the DC output voltage and each set control signal; and the current mode controller supplying the switching signal to define and control the time width of the pulses of input current in a predetermined relation to each set control signal and the DC output voltage.

5. A method of creating an output RF electrosurgical waveform for application in electrosurgery from a source of input DC energy, comprising:

creating pulses of input current from the input DC energy source;

establishing an energy content of each pulse of input current by controlling a time width of each pulse of input current;

converting the energy content of the pulses of input current into a DC output voltage having a magnitude related to the energy content of the pulses of input current;

delivering the pulses of input current for conversion at a selected one of a plurality of different rates;

selecting the one of the plurality of different rates for delivering the pulses of input current in relation to the magnitude of the DC output voltage;

creating energizing pulses having an energy content established by the DC output voltage and a time width; and converting the energy content of the energizing pulses into the output RF electrosurgical waveform.

6. A method as defined in claim 5, further comprising:

deriving an input current sense signal related to the pulses of input current, the input current sense signal having an initial anomalous portion and a remaining portion;

suppressing the initial anomalous portion of the input current sense signal;

supplying the remaining portion of the input current sense signal as a feedback current sense signal; and regulating the time width of each pulse of input current in relation to the feedback current sense signal.

7. A method as defined in claim 6, further comprising:

regulating the time width of each pulse of input current also in relation to the magnitude of the DC output voltage.

8. A method as defined in claim 5, further comprising:

regulating the time width of each energizing pulse to control a power characteristic of the output RF electrosurgical waveform;

regulating the time width of each pulse of input current to maintain the DC output voltage essentially constant as the power characteristic of the output RF electrosurgical waveform varies.

9. A method as defined in claim 8, further comprising:

selecting one output RF electrosurgical waveform from among a plurality of output RF electrosurgical waveforms for application in electrosurgery;

selecting the power characteristic of the selected one output RF electrosurgical waveform; and regulating the time width of the each pulse of input current in relation to the selected one output RF electrosurgical waveform and the selected power characteristic of the selected one output RF electrosurgical waveform.

10. A method as defined in claim 9, further comprising:

adjusting the time width of each pulse of input current to create a predetermined magnitude of the DC output voltage which is different for each of at least a plurality of the selected output RF electrosurgical waveforms and the selected power characteristics of the selected output RF electrosurgical waveform.

11. A method of creating an output RF electrosurgical waveform for application in electrosurgery from a source of input DC energy, comprising:

creating pulses of input current from the input DC energy source;

establishing an energy content of each pulse of input current by controlling a time width of each pulse of input current;

converting the energy content of the pulses of input current into a DC output voltage having a magnitude related to the energy content of the pulses of input current;

delivering the pulses of input current for conversion at a selected one of a plurality of different rates;

selecting the one of the plurality of different rates for delivering the pulses of input current in relation to the magnitude of the DC output voltage;

delivering the pulses of input current for conversion at a predetermined higher rate in relation to a relatively higher value of the DC output voltage and at a predetermined lower rate in relation to a relatively lower value of the DC output voltage;

creating energizing pulses having an energy content established by the DC output voltage and a time width; and converting the energy content of the energizing pulses into the output RF electrosurgical waveform.

12. A method as defined in claim 11, further comprising:

changing the rate at which the pulses of input current are delivered for conversion from the predetermined lower rate to the predetermined higher rate at a first predetermined DC output voltage; and changing the rate at which the pulses of input current are delivered for conversion from the predetermined higher rate to the predetermined lower rate at a second predetermined DC output voltage which is different from the first predetermined DC output voltage.

13. A method as defined in claim 12, further comprising:
establishing the first predetermined DC output voltage to be greater than the second predetermined DC output voltage.

14. A method as defined in claim 11, further comprising:
deriving an input current sense signal related to the pulses of input current, the input current sense signal having an initial anomalous portion and a remaining portion;
suppressing the initial anomalous portion of the input current sense signal;
supplying the remaining portion of the input current sense signal as a feedback current sense signal; and
regulating the time width of each pulse of input current in relation to the feedback current sense signal.

15. A method as defined in claim 14, further comprising:
selecting one output RF electrosurgical waveform from among a plurality of output RF electrosurgical waveforms for application in electrosurgery;
selecting the power characteristic of the selected one output RF electrosurgical waveform; and
regulating the time width of the each pulse of input current also in relation to the selected one output RF electrosurgical waveform and the selected power characteristic of the selected one output RF electrosurgical waveform.

16. A method as defined in claim 11, further comprising:
regulating the time width of each energizing pulse to control a power characteristic of the output RF electrosurgical waveform;
regulating the time width of each pulse of input current to maintain the DC output voltage essentially constant as the power characteristic of the output RF electrosurgical waveform varies.

17. A method as defined in claim 16, further comprising:
selecting one output RF electrosurgical waveform from among a plurality of output RF electrosurgical waveforms for application in electrosurgery;
selecting the power characteristic of the selected one output RF electrosurgical waveform; and
regulating the time width of the each pulse of input current in relation to the selected one output RF electrosurgical waveform and the selected power characteristic of the selected one output RF electrosurgical waveform.

18. A method as defined in claim 17, further comprising:
adjusting the time width of each pulse of input current to create a predetermined magnitude of the DC output voltage which is different for each of at least a plurality of the selected output RF electrosurgical waveforms and the selected power characteristics of the selected output RF electrosurgical waveform.

19. A method of creating an output RF electrosurgical waveform for application in electrosurgery from a source of input DC energy, comprising:
creating pulses of input current from the input DC energy source;
establishing an energy content of each pulse of input current by controlling a time width of each pulse of input current;
converting the energy content of the pulses of input current into a DC output voltage having a magnitude related to the energy content of the pulses of input current;
deriving an input current sense signal related to the pulses of input current, the input current sense signal having an initial anomalous portion and a remaining portion;
suppressing the initial anomalous portion of the input current sense signal;
supplying the remaining portion of the input current sense signal as a feedback current sense signal;
regulating the time width of each pulse of input current in relation to the feedback current sense signal;
regulating the time width of each pulse of input current in relation to the magnitude of the DC output voltage;
delivering the pulses of input current for conversion at a selected on of a plurality of different rates;
selecting the one of the plurality of different rates for delivering the pulses of input current in relation to the magnitude of the DC output voltage;
delivering the pulses of input current for conversion at a predetermined higher rate in relation to a relatively higher value of the DC output voltage and at a predetermined lower rate in relation to a relatively lower value of the DC output voltage;
creating energizing pulses having an energy content established by the DC output voltage and a time width; and
converting the energy content of the energizing pulses into the output RF electrosurgical waveform.

20. A method as defined in claim 19, further comprising:
selecting one output RF electrosurgical waveform from among a plurality of output RF electrosurgical waveforms for application in electrosurgery;
selecting the power characteristic of the selected one output RF electrosurgical waveform; and
regulating the time width of the each pulse of input current also in relation to the selected one output RF electrosurgical waveform and the selected power characteristic of the selected one output RF electrosurgical waveform.

21. A method as defined in claim 19, further comprising:
changing the rate at which the pulses of input current are delivered for conversion from the predetermined lower rate to the predetermined higher rate at a first predetermined DC output voltage; and
changing the rate at which the pulses of input current are delivered for conversion from the predetermined higher rate to the predetermined lower rate at a second predetermined DC output voltage which is different from the first predetermined DC output voltage.

22. A method as defined in claim 21, further comprising:
establishing the first predetermined DC output voltage to be greater than the second predetermined DC output voltage.

* * * * *